(12) United States Patent
Nomoto et al.

(10) Patent No.: US 10,994,043 B2
(45) Date of Patent: May 4, 2021

(54) FRAGRANCE PROVIDING DEVICE

(71) Applicant: Sony Corporation, Tokyo (JP)

(72) Inventors: Koya Nomoto, Aichi (JP); Shuji Fujita, Tokyo (JP); Yukari Tsunoda, Tokyo (JP); Tsunetoshi Samukawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 475 days.

(21) Appl. No.: 15/768,703

(22) PCT Filed: Jul. 25, 2016

(86) PCT No.: PCT/JP2016/071755
§ 371 (c)(1),
(2) Date: Apr. 16, 2018

(87) PCT Pub. No.: WO2017/068829
PCT Pub. Date: Apr. 27, 2017

(65) Prior Publication Data
US 2018/0303964 A1    Oct. 25, 2018

(30) Foreign Application Priority Data

Oct. 23, 2015    (JP) .............................. JP2015-208660

(51) Int. Cl.
*A61L 9/12*    (2006.01)
(52) U.S. Cl.
CPC .................. *A61L 9/125* (2013.01); *A61L 9/12* (2013.01); *A61L 2209/134* (2013.01)
(58) Field of Classification Search
CPC ....... A61L 9/125; A61L 9/12; A61L 2209/134
See application file for complete search history.

(56) References Cited

FOREIGN PATENT DOCUMENTS

| CN | 102245413 A | 11/2011 |
|---|---|---|
| CN | 203089984 U | 7/2013 |
| CN | 204395064 U | 6/2015 |
| EP | 2 347 922 A2 | 7/2011 |
| JP | 63-100048 U | 6/1988 |
| JP | 3-234262 A | 10/1991 |

(Continued)

OTHER PUBLICATIONS

Japanese Office Action dated Oct. 23, 2019 in connection with Japanese Application No. 2015-208660 and English translation thereof.

(Continued)

*Primary Examiner* — Sean E Conley
(74) *Attorney, Agent, or Firm* — Wolf, Greenfield & Sacks, P.C.

(57) ABSTRACT

[Object] To propose a novel and improved fragrance providing device that can be reduced in size.
[Solution] Provided is a fragrance providing device including: a fragrance material holding member in which a plurality of holding passages each holding a fragrance material are provided to penetrate the fragrance material holding member; and a rotation mechanism capable of relatively rotating the fragrance material holding member and a member provided with an introduction port that communicates with part of the plurality of holding passages and introduces air supplied from an airflow source to the part of the holding passages, in a manner that the part of the holding passages that communicates with the introduction port is switched.

16 Claims, 14 Drawing Sheets

(56) References Cited

FOREIGN PATENT DOCUMENTS

| | | |
|---|---|---|
| JP | 03-234262 A | 10/1991 |
| JP | 04-208161 A | 7/1992 |
| JP | 4-208161 A | 7/1992 |
| JP | 04-128750 U | 11/1992 |
| JP | 05-009552 U | 2/1993 |
| JP | 05-056017 U | 7/1993 |
| JP | 05-082442 U | 11/1993 |
| JP | 11-501834 A | 2/1999 |
| JP | 2002-065832 A | 3/2002 |
| JP | 2013-094436 A | 5/2013 |
| JP | 2013-167741 A | 8/2013 |
| TW | 323231 B | 12/1997 |
| WO | WO 96/28195 A1 | 9/1996 |

OTHER PUBLICATIONS

Extended European Search Report dated Oct. 15, 2018 in connection with European Application No. 16857147.9.
International Search Report and English translation thereof dated Oct. 25, 2016 in connection with International Application No. PCT/JP2016/071755.
Chinese Office Action dated Feb. 3, 2020 in connection with Chinese Application No. 201680060530.2, and English translation thereof.
Written Opinion and English translation thereof dated Oct. 25, 2016 in connection with International Application No. PCT/JP2016/071755.
International Preliminary Report on Patentability and English translation thereof dated May 3, 2018 in connection with International Application No. PCT/JP2016/071755.

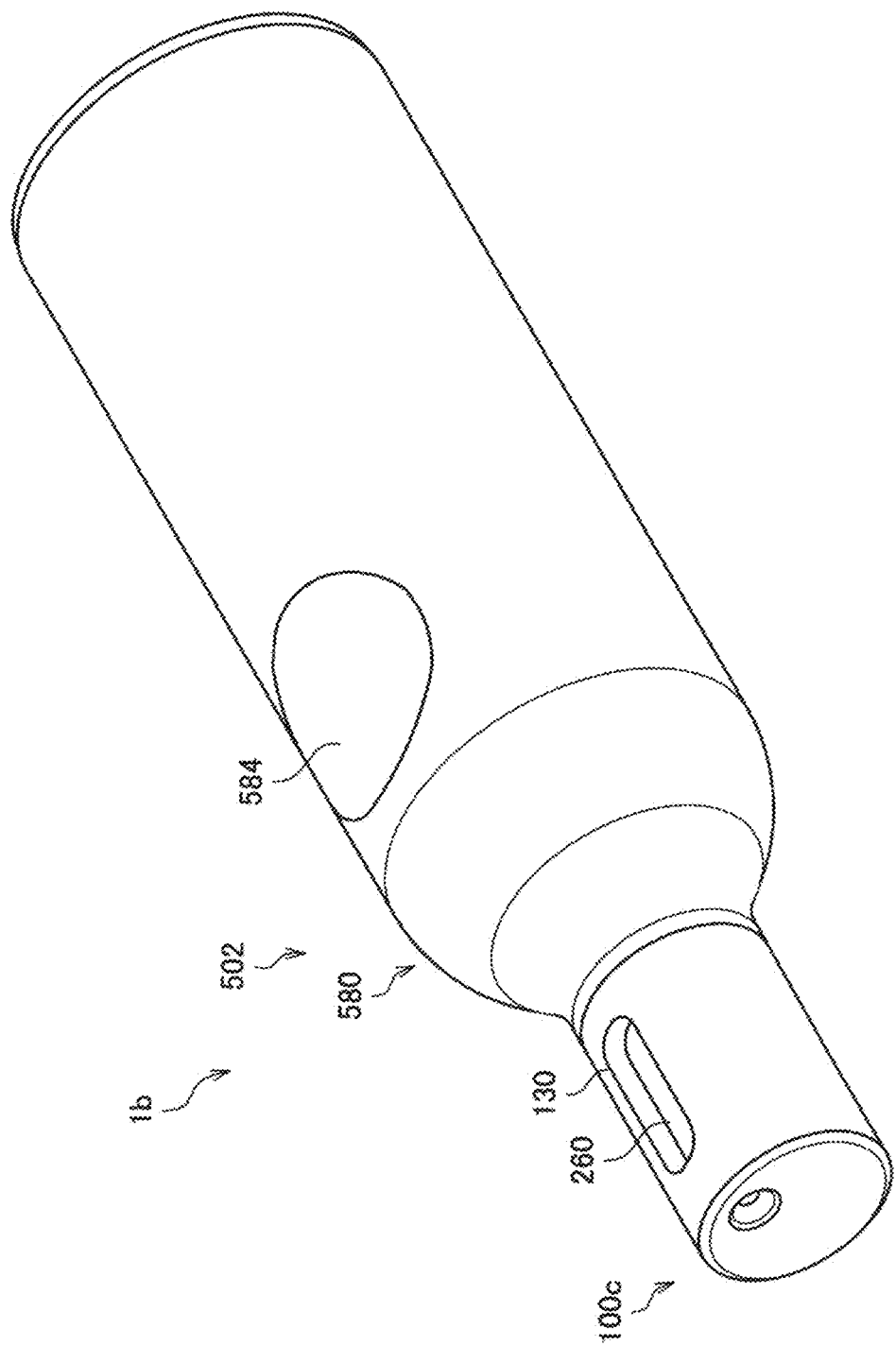

FRAGRANCE PROVIDING DEVICE

CROSS REFERENCE TO RELATED APPLICATIONS

This application claims the benefit under 35 U.S.C. § 371 as a U.S. National Stage Entry of International Application No. PCT/JP2016/071755, filed in the Japanese Patent Office as a Receiving Office on Jul. 25, 2016, which claims priority to Japanese Patent Application Number JP2015-208660, filed in the Japanese Patent Office on Oct. 23, 2015, each of which is hereby incorporated by reference in its entirety.

TECHNICAL FIELD

The present disclosure relates to a fragrance providing device.

BACKGROUND ART

In recent years, technologies related to a fragrance providing device having a plurality of spaces each holding a fragrance material have been proposed, for purposes such as providing a plurality of types of fragrances. Such a fragrance providing device can provide a plurality of fragrances by, for example, causing a plurality of spaces to hold different types of fragrance materials.

For example, for the purpose of reducing the size of the device itself, Patent Literature 1 discloses an olfactory display which presents a fragrance within a range bounded in terms of time and space, including: a housing having an emitting port; a plurality of fragrance chambers formed by partitioning an internal space of the housing with the partitioning walls; a solid-like fragrance source accommodated in at least one of the fragrance chambers; a plurality of airflow sources each of which is provided in each of the fragrance chambers and sends an air into the fragrance chamber by using a diaphragm provided with a piezoelectric element; and a plurality of fragrance passages each extending from the fragrance chambers toward the emitting port, in which the plurality of fragrance passages are joined to each other in a position near the emitting port to form a single common passage and Venturi tube structure is formed at the joining portion.

CITATION LIST

Patent Literature

Patent Literature 1: JP 2013-167741A

DISCLOSURE OF INVENTION

Technical Problem

In the technology disclosed in Patent Literature 1, since an airflow source is provided for each of a plurality of spaces each holding a fragrance material, in the case where the number of spaces holding fragrance materials is increased for purposes such as increasing the types of providable fragrances, an increase in the size of the device may be caused by the increase in the number of airflow sources. Therefore, it seems to be desirable that a fragrance providing device having a plurality of spaces each holding a fragrance material be further reduced in size.

Hence, the present disclosure proposes a novel and improved fragrance providing device that can be reduced in size.

Solution to Problem

According to the present disclosure, there is provided a fragrance providing device including: a fragrance material holding member in which a plurality of holding passages each holding a fragrance material are provided to penetrate the fragrance material holding member; and a rotation mechanism capable of relatively rotating the fragrance material holding member and a member provided with an introduction port that communicates with part of the plurality of holding passages and introduces air supplied from an airflow source to the part of the holding passages, in a manner that the part of the holding passages that communicates with the introduction port is switched.

Advantageous Effects of Invention

As described above, according to the present disclosure, the device can be reduced in size.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 14 is an explanatory diagram illustrating an example of a configuration of a fragrance providing device according to a second modification example.

MODE(S) FOR CARRYING OUT THE INVENTION

Figure 1:
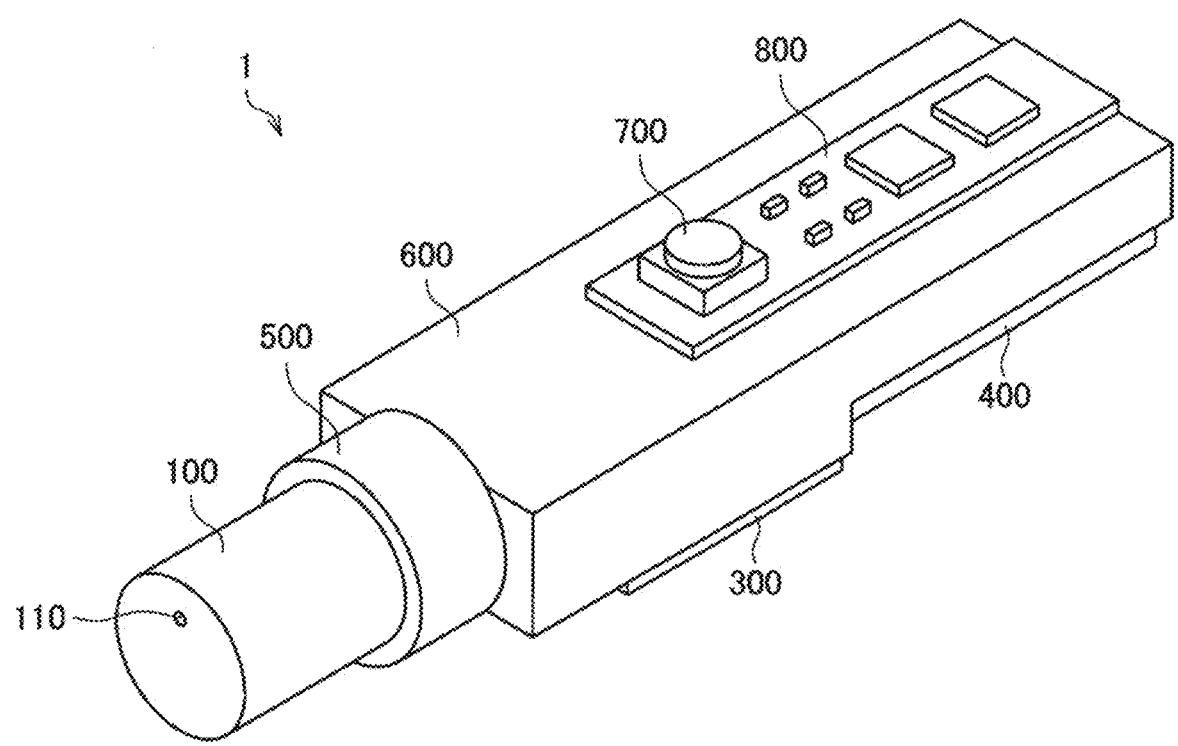
FIG. 1 is a perspective view of an example of a fragrance providing device according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
1. Fragrance providing device
2. Rotation mechanism
2-1. First example
2-2. Second example
3. Modification examples
4. Conclusion

1. FRAGRANCE PROVIDING DEVICE

Figure 2:
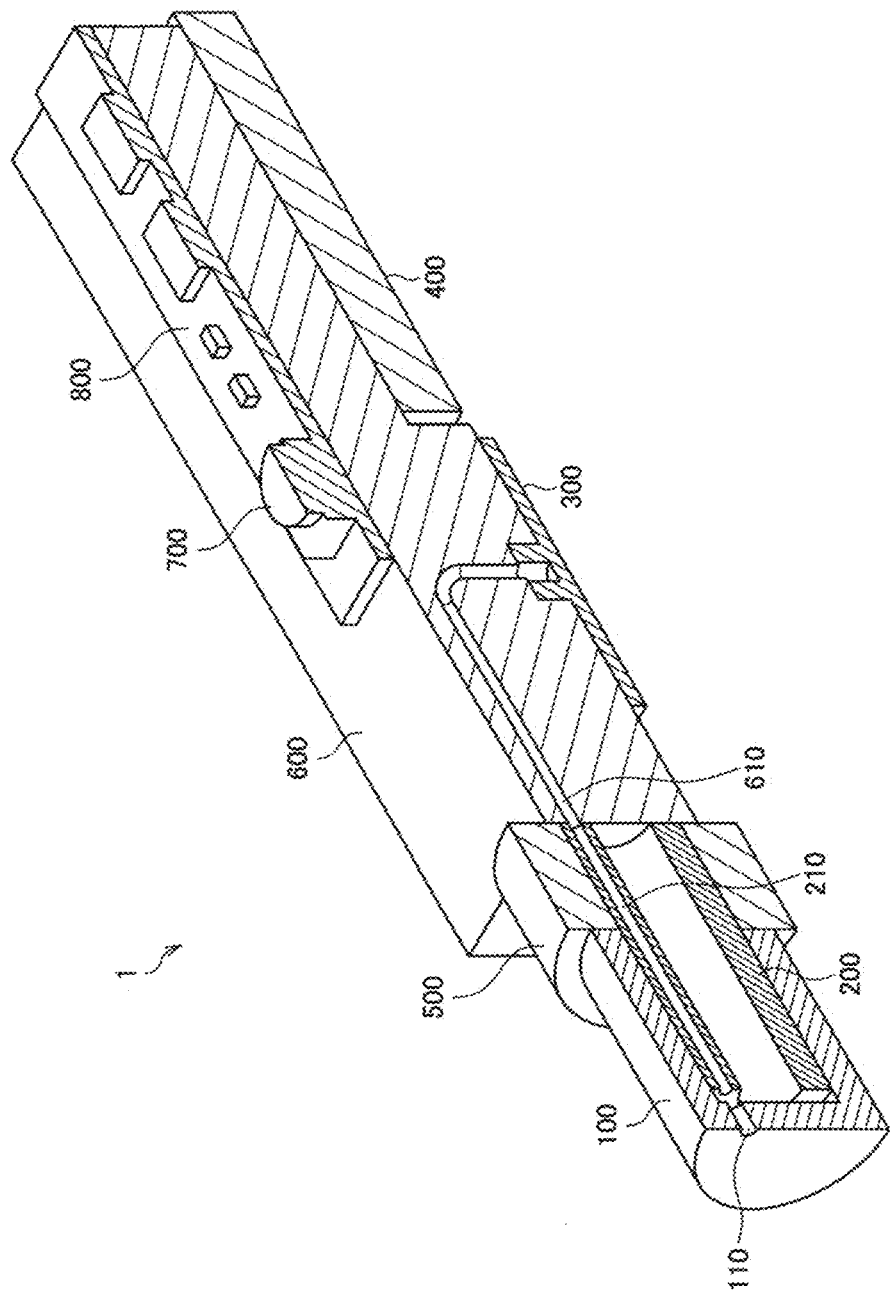
FIG. 2 is a cross-sectional perspective view of an example of the fragrance providing device according to the embodiment.
Figure 3:
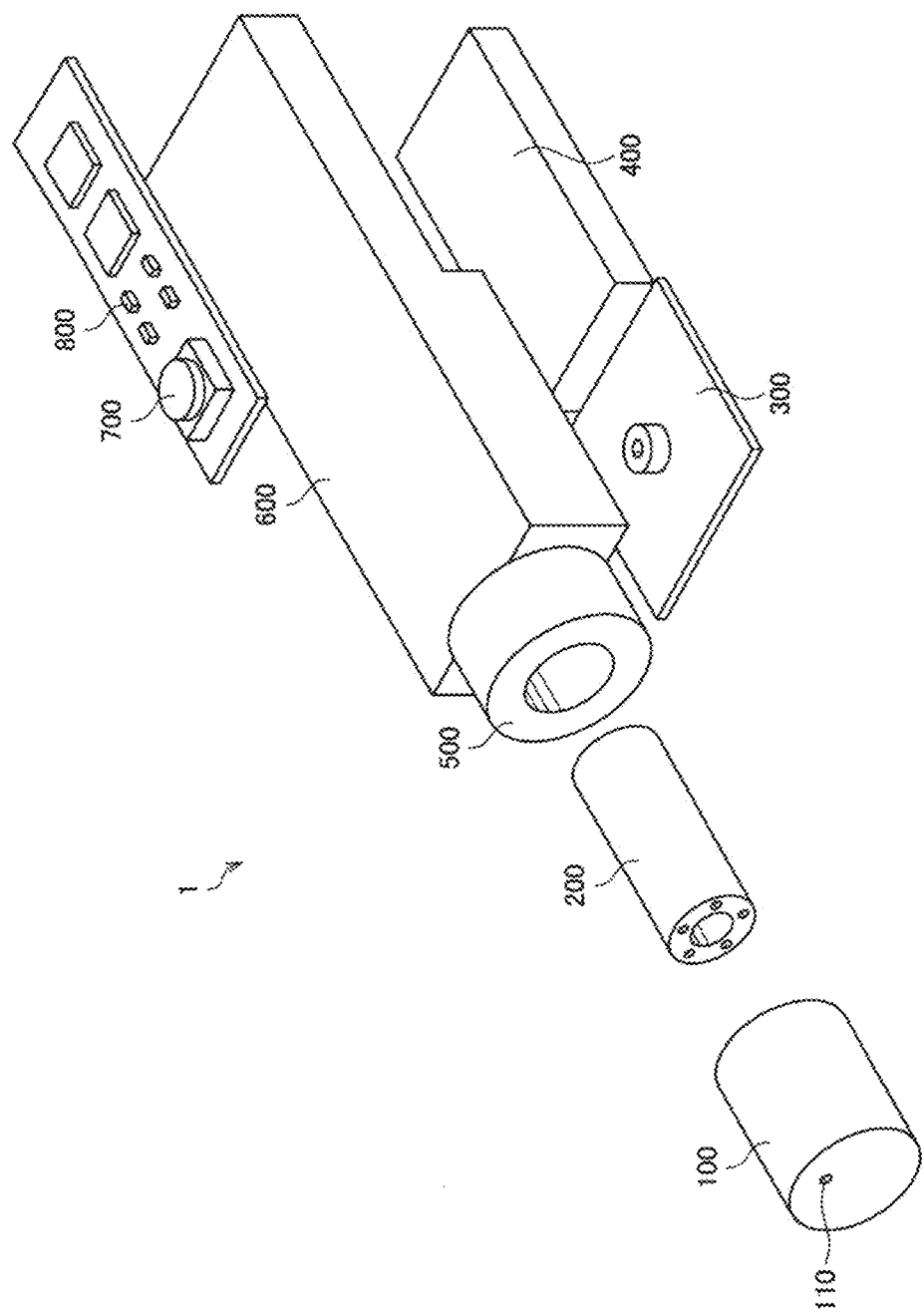
FIG. 3 is an exploded perspective view of an example of the fragrance providing device according to the embodiment.

First, a fragrance providing device 1 according to the present embodiment is described with reference to FIGS. 1 to 5. FIG. 1 is a perspective view of an example of the fragrance providing device 1 according to the present embodiment. FIG. 2 is a cross-sectional perspective view of an example of the fragrance providing device 1 according to the present embodiment. FIG. 3 is an exploded perspective view of an example of the fragrance providing device 1 according to the present embodiment. Note that in the following description, the side on which a discharge port 110 of a lid 100 is disposed in the fragrance providing device 1 is called a front end side.

As illustrated in FIGS. 1 to 3, the fragrance providing device 1 according to the present embodiment includes the lid 100, a fragrance material holding member 200, an air pump 300, a battery 400, a rotation mechanism 500, a chassis 600, a switch 700, and a substrate 800.

The lid 100 is a member that separates the fragrance material holding member 200 from the outside. The lid 100 has, for example, a tubular shape that is open on a rear end side, as illustrated in FIGS. 1 to 3. On the front end side of the lid 100 is provided the discharge port 110 from which air including a vaporized fragrance material sent from the fragrance material holding member 200 is discharged. The discharge port 110 is provided to communicate with a front end part of a holding passage 210 through which air is supplied among a plurality of holding passages 210 provided in the fragrance material holding member 200. An inner diameter of the discharge port 110 may be larger than an inner diameter of the holding passage 210.

The fragrance material holding member 200 is a member that holds a fragrance material. The fragrance material holding member 200 has, for example, a hollow tubular shape as illustrated in FIGS. 2 and 3. In the fragrance material holding member 200, the plurality of holding passages 210 each holding a fragrance material are provided to penetrate the fragrance material holding member 200. The fragrance material is, for example, held in a state of adhering to an inner surface of the holding passage 210. Specifically, the fragrance material may be an essential oil, an essential oil diluted in ethanol, or the like.

The plurality of holding passages 210 are provided at equal intervals on a circumference around a central axis of the fragrance material holding member 200, for example, and are provided in a straight-line from the rear end side to the front end side. Air supplied from the air pump 300 is sent to part of the plurality of holding passages 210. This causes flow of air from the rear end side to the front end side of the holding passage 210. Then, a vaporized component of the fragrance material held by the holding passage 210 is discharged from the discharge port 110 of the lid 100. FIG. 2 illustrates a flow channel 610 of the chassis 600 as an air flow channel between the air pump 300 and the holding passage 210; however, another flow channel may be present between the flow channel 610 of the chassis 600 and the holding passage 210. Details of the air flow channel between the air pump 300 and the holding passage 210 will be given later.

Examples of a constituent material of the holding passage 210 include a resin such as an acrylic resin, a urethane resin, an ABS resin, polyetheretherketone (PEEK), polyacetal (POM), a silicone resin, a fluorine resin, an olefin polymer resin, or a polyimide resin, a metal such as stainless steel, and glass. Specifically, a constituent material of the holding passage 210 may be selected in consideration of chemical resistance, weather resistance, strength, and the like. The inner diameter of the holding passage 210 may be set to a value smaller than 1 mm, as an example. The holding passage 210 that is a micro flow channel having such a small inner diameter may be produced by laminate molding using a 3D printer, for example.

As the inner diameter of the holding passage 210 is smaller, the occurrence of turbulent flow of a fluid in the holding passage 210 is suppressed more easily and the flow of the fluid is more likely to be a laminar flow. In addition, in the case where the output of the air pump 300 is constant, as the inner diameter of the holding passage 210 is smaller, air flows faster in the holding passage 210. Thus, in the fragrance providing device 1 according to the present embodiment, straightness of air including the vaporized component of the fragrance material discharged from the discharge port 110 is improved. Therefore, by causing the air including the vaporized component of the fragrance material to be discharged toward a user of the fragrance providing device 1, the user can be provided with a fragrance without influence on the user's surroundings.

In addition, as the inner diameter of the holding passage 210 is smaller, the proportion of an area in which the fragrance material is held with respect to an area in which air passes is larger in a transverse section in the holding passage 210, and thus, the proportion of the fragrance material included in the air that passes through the holding passage 210 and is discharged from the discharge port 110 is larger. This enables a fragrance to be provided to the user more reliably. In addition, dimensions of the entire device can be reduced by making the inner diameter of the holding passage 210 smaller, which enables a reduction in the weight of the entire device. Therefore, the fragrance providing device 1 can be carried easily.

The air pump 300 is an example of an airflow source according to the present disclosure. For example, the air pump 300 supplies air to part of the plurality of holding passages 210 via the flow channel 610 and another flow channel (not illustrated). The air pump 300 is, for example, electrically connected to the battery 400 via the substrate 800, and is driven by electric power supplied from the battery 400. Specifically, the air pump 300 includes a diaphragm to which a piezoelectric element is attached, and performs air blowing by deforming the diaphragm by application of an alternating current to the piezoelectric element. Note that the type of air blowing of the air pump 300 is not limited to this example, and for example, may be a fin type, a cylinder type, or the like. In addition, the air pump 300 may be of a manual type, in which case the battery 400, the switch 700, and the substrate 800 may be omitted from the configuration of the fragrance providing device 1.

The battery 400 stores electric power for operating the air pump 300. The battery 400 may be a primary battery capable of only discharging, or may be a secondary battery capable of charging as well.

The rotation mechanism 500 is capable of relatively rotating the fragrance material holding member 200 and a member provided with an introduction port that communicates with part of the plurality of holding passages 210 and introduces the air supplied from the air pump 300 to part of the holding passages 210, in a manner that part of the holding passages 210 that communicates with the introduction port is switched. The rotation mechanism 500 illustrated in FIGS. 1 to 3 is a conceptual diagram, and details of the rotation mechanism 500 will be given later.

The chassis 600 is provided with the air pump 300, the battery 400, the rotation mechanism 500, and the substrate 800. In addition, the chassis 600 may be provided with wiring that electrically connects components, as necessary.

The switch 700 is provided on the substrate 800 to switch a drive state of the air pump 300. The substrate 800 is electrically connected to the battery 400, and for example, when the switch 700 is pressed by the user, electric conduction to a drive circuit for driving the air pump 300 that is installed on the substrate 800 is performed. Thus, the drive state of the air pump 300 is switched in accordance with the state of pressing of the switch 700 by the user.

Figure 4:
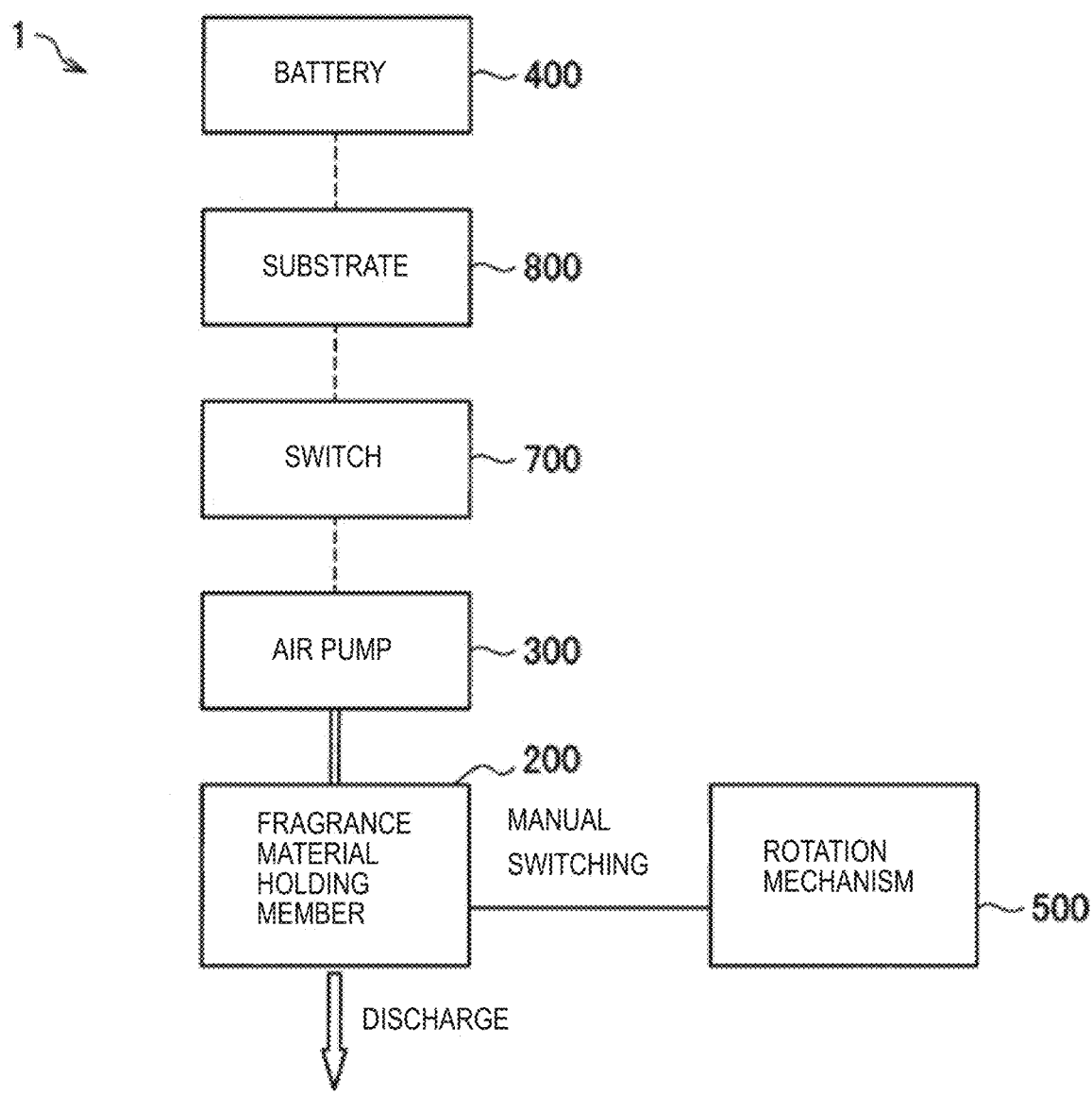
FIG. 4 is a system block diagram illustrating an example of the fragrance providing device according to the embodiment.

FIG. 4 is a system block diagram illustrating an example of the fragrance providing device 1 according to the present embodiment. As illustrated in FIG. 4, the battery 400 and the substrate 800 are electrically connected to each other. Then, when the switch 700 is pressed, electric conduction to the drive circuit for driving the air pump 300 that is installed on the substrate 800 is performed, and the air pump 300 is driven. Thus, the air pump 300 starts air blowing, and the air supplied from the air pump 300 is sent to the holding passage 210 of the fragrance material holding member 200. Then, the vaporized component of the fragrance material held by the holding passage 210 of the fragrance material holding member 200 is discharged to the outside from the discharge port 110 of the lid 100. Switching of the holding passage 210 to which air is introduced among the plurality of holding passages 210 of the fragrance material holding member 200 by the rotation mechanism 500 is performed manually.

Figure 5:
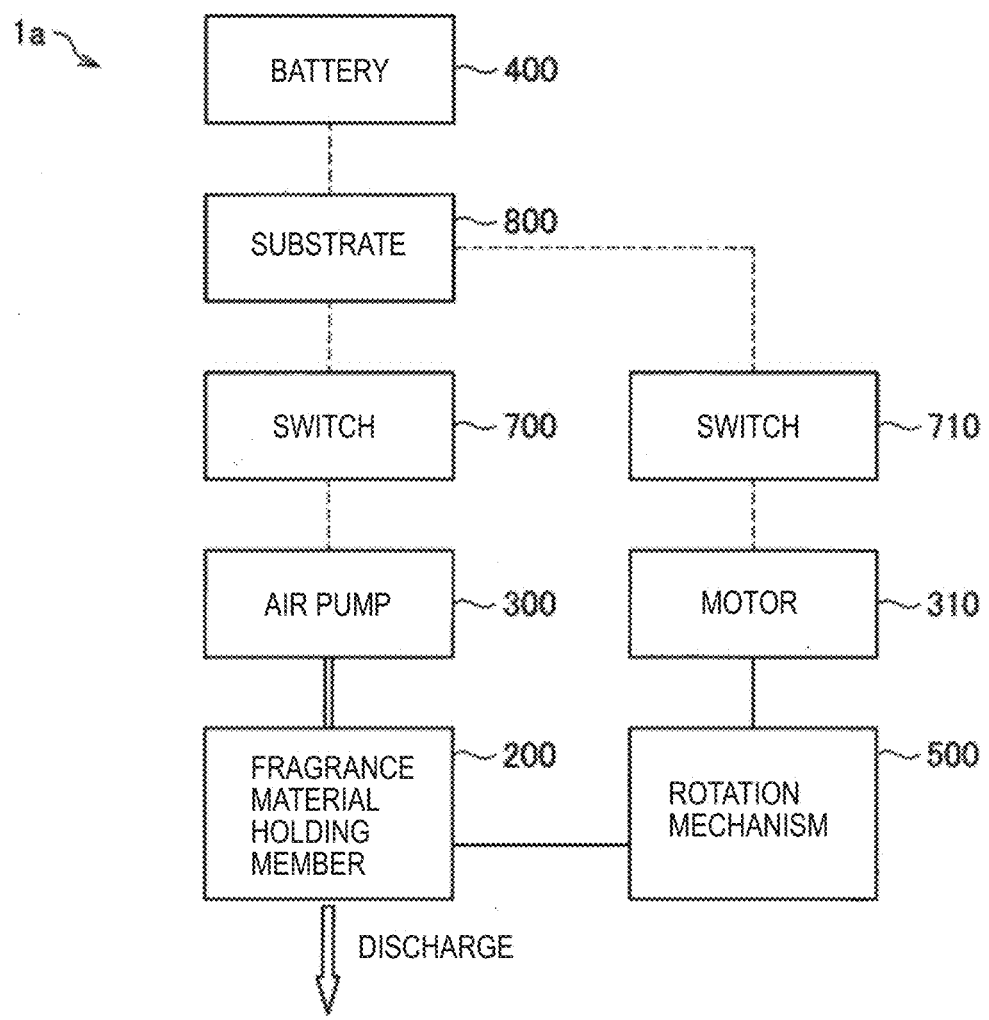
FIG. 5 is a system block diagram illustrating an example of a fragrance providing device according to another embodiment.

In this specification, the fragrance providing device 1 in which switching of the holding passage 210 to which air is introduced by the rotation mechanism 500 is performed manually is mainly described, as described using FIG. 4; however, the type of switching by the rotation mechanism 500 is not limited to this example, and for example, the rotation mechanism 500 may be driven by a motor. Such a fragrance providing device 1a according to another embodiment includes a motor 310 that drives the rotation mechanism 500, and a switch 710 that switches electric conduction to a drive circuit for driving the motor 310 that is installed on the substrate 800. According to the fragrance providing device 1a, for example, as illustrated in FIG. 5, when the switch 710 is pressed, electric conduction to the drive circuit for driving the motor 310 that is installed on the substrate 800 is performed, and the motor 310 is driven. Thus, the rotation mechanism 500 is driven by the motor 310, and switching of the holding passage 210 to which air is introduced among the plurality of holding passages 210 of the fragrance material holding member 200 by the rotation mechanism 500 is performed.

2. ROTATION MECHANISM 2-1. First Example

Figure 6:
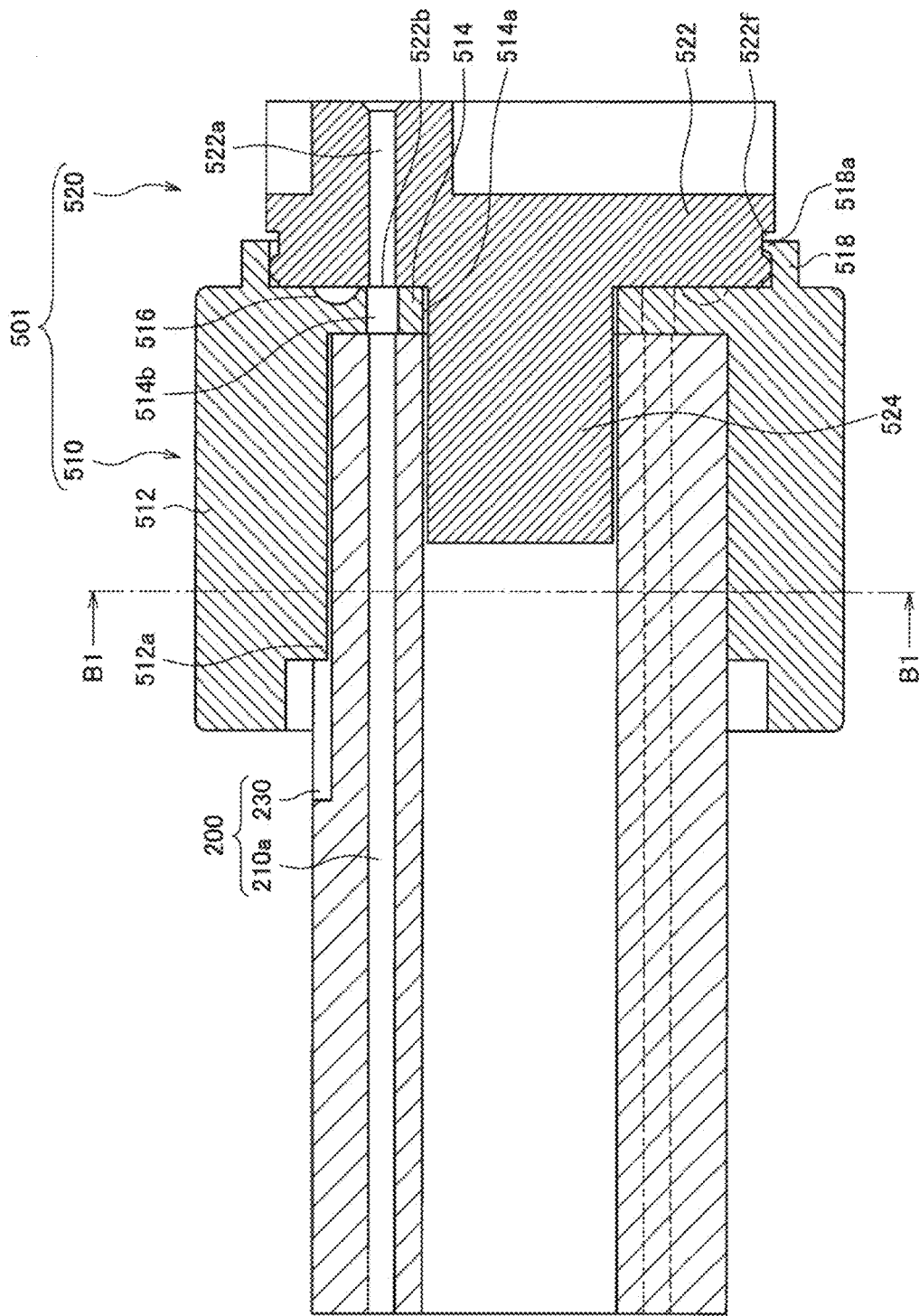
FIG. 6 is an explanatory diagram illustrating an example of a configuration of a fragrance material holding member and a rotation mechanism according to a first example.
Figure 7:
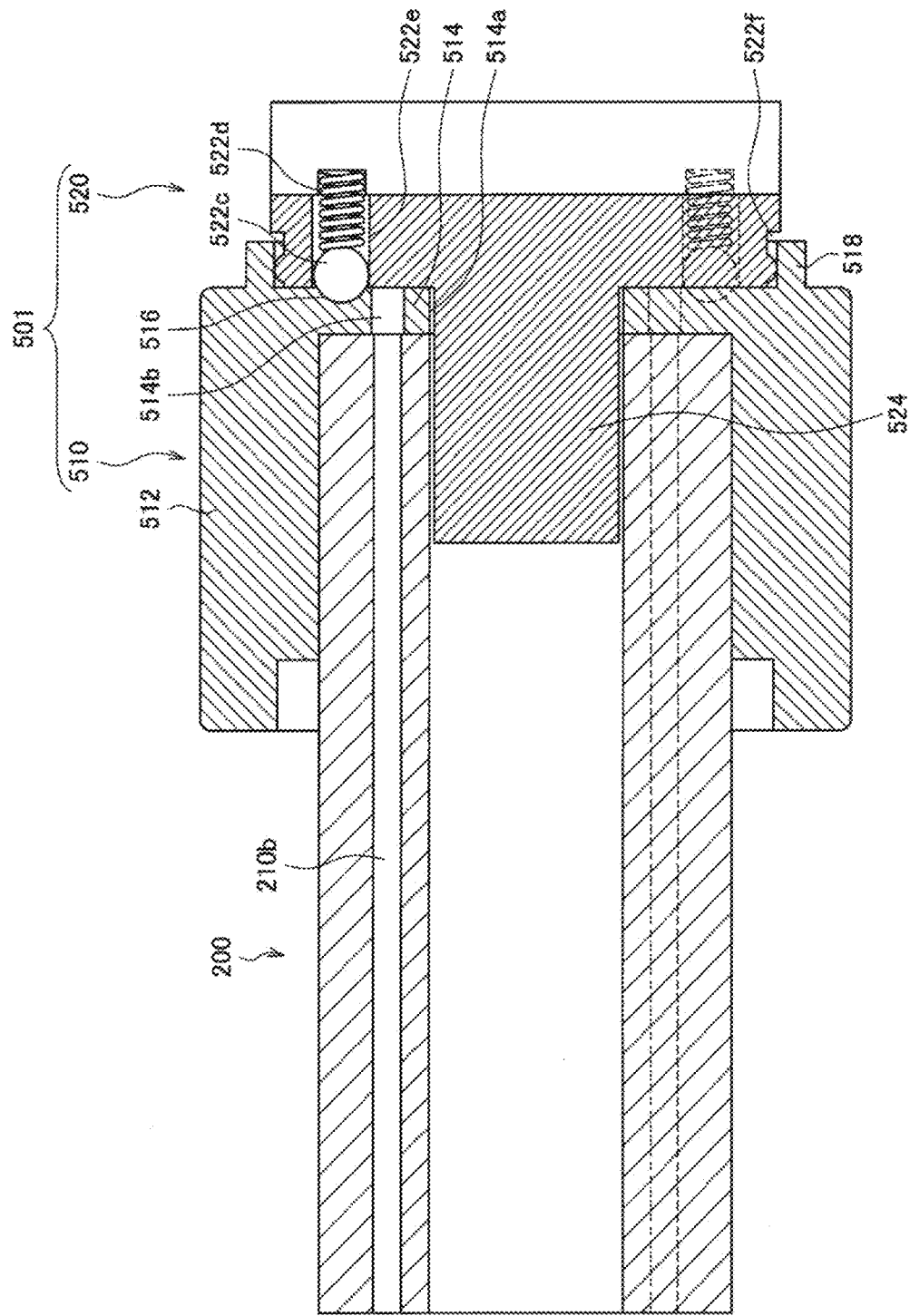
FIG. 7 is an explanatory diagram illustrating the example of the configuration of the fragrance material holding member and the rotation mechanism according to the first example.
Figure 8:
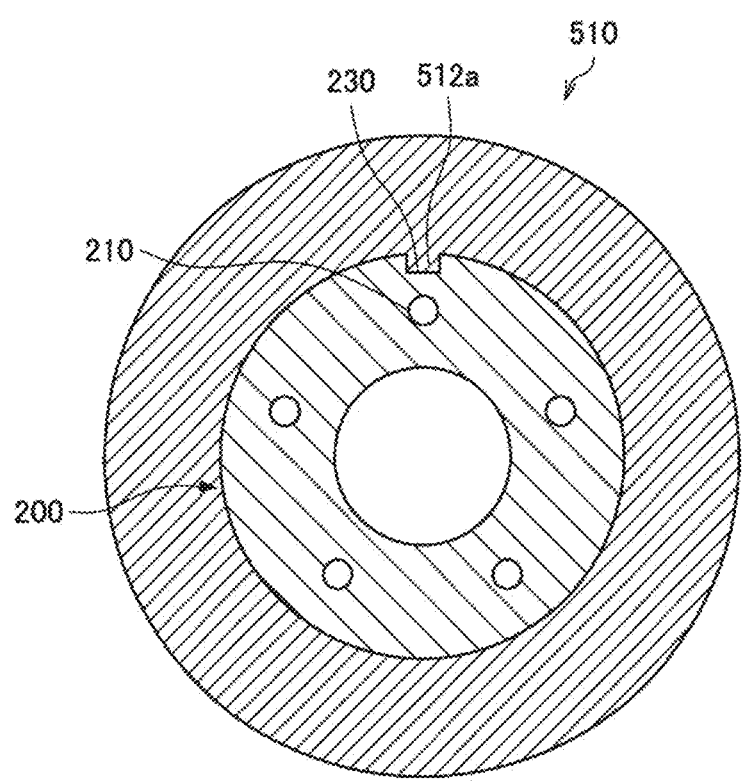
FIG. 8 is a cross-sectional view of an example of a B1-B1 cross-section illustrated in FIG. 6.

Now, a rotation mechanism 501 according to a first example will be described with reference to FIGS. 6 to 8. FIGS. 6 and 7 are explanatory diagrams illustrating an example of a configuration of the fragrance material holding member 200 and the rotation mechanism 501 according to the first example. FIG. 6 is a cross-sectional view along a cross-section passing through a holding passage 210a to which the air supplied from the air pump 300 is sent, and FIG. 7 is a cross-sectional view along a cross-section passing through a holding passage 210b to which the air supplied from the air pump 300 is not sent. FIG. 8 is a cross-sectional view of an example of a B1-B1 cross-section illustrated in FIG. 6. As illustrated in FIGS. 6 and 7, the rotation mechanism 501 according to the first example includes a rotation transfer unit 510 and an air introduction unit 520. The rotation mechanism 501 according to the first example is configured in a manner that rotation of the rotation transfer unit 510 is transferred to the fragrance material holding member 200. In addition, the fragrance material holding member 200 and the rotation transfer unit 510 are rotatable with respect to the air introduction unit 520. Details of such a rotation mechanism 501 are described below.

The air introduction unit 520 includes a large diameter part 522 located on the rear end side and a small diameter part 524 that is provided on a central part of the front end side of the large diameter part 522 and projects in a front end direction. The large diameter part 522 and the small diameter part 524 each have a substantially cylindrical shape, for example. The large diameter part 522 is provided with a flow channel 522a for guiding the air supplied from the air pump 300 to the holding passage 210a. For example, a rear end part of the flow channel 522a communicates with a front end part of the flow channel 610 of the chassis 600 illustrated in FIG. 2. Thus, the air supplied from the air pump 300 is sent to the flow channel 522a via the flow channel 610. A front end part of the flow channel 522a is provided with an introduction port 522b that communicates with the holding passage 210a and introduces the air supplied from the air pump 300 to the holding passage 210a. The introduction port 522b may communicate with the holding passage 210a via another flow channel, and for example, may communicate with the holding passage 210a via a flow channel 514b provided in the rotation transfer unit 510, as illustrated in FIG. 6.

The rotation transfer unit 510 includes a tubular part 512 that holds an outer circumferential part of the rear end side of the fragrance material holding member 200, and a bottom part 514 that is provided on the inner circumference side of a rear end part of the tubular part 512 and holds a rear end part of the fragrance material holding member 200. The fragrance material holding member 200 is fitted to an inner circumferential part of the tubular part 512. Note that the shape of the tubular part 512 is not particularly limited, and may be any shape fittable to the fragrance material holding member 200. Movement of the fragrance material holding member 200 in the axial direction with respect to the rotation transfer unit 510 is constrained by, for example, lightly press-fitting the fragrance material holding member 200 to the tubular part 512. Note that in order to constrain the movement of the fragrance material holding member 200 in the axial direction with respect to the rotation transfer unit 510 more reliably, a mechanism that urges an outer circumferential part of the tubular part 512 to the inner circumferential part side may be applied.

A front end part of the bottom part 514 faces the rear end part of the fragrance material holding member 200, and a rear end part of the bottom part 514 faces a step between the large diameter part 522 and the small diameter part 524 of the air introduction unit 520. At the center of the bottom part 514 may be provided an opening 514a that communicates with an inner circumferential part of the fragrance material holding member 200, and the small diameter part 524 of the air introduction unit 520 may be inserted into the opening 514a of the bottom part 514 and the inside of the inner circumferential part of the fragrance material holding member 200. The small diameter part 524 is used as, for example, a guide for facilitating assembly of the fragrance material holding member 200 and the rotation mechanism 501. Therefore, the small diameter part 524 may be omitted from the configuration of the rotation mechanism 501. In addition, in the case where the small diameter part 524 functions as a guide, the small diameter part 524 may have a shape such as a polygonal column or an elliptic cylinder, as long as the shape is relatively rotatable with respect to the fragrance material holding member 200 and the rotation transfer unit 510. In the bottom part 514, flow channels 514b that communicate with the respective holding passages 210 of the fragrance material holding member 200 are provided to penetrate the bottom part 514.

The inner circumferential part of the tubular part 512 is provided with a locking projection 512a projecting inwardly. The locking projection 512a is provided to extend along the axial direction of the tubular part 512, for example. As illustrated in FIGS. 6 and 8, the locking projection 512a is fitted to a locking groove 230 provided on an outer circumferential part of the fragrance material holding member 200 to extend along the axial direction of the fragrance material holding member 200. Thus, rotation of the rotation transfer unit 510 is transferred to the fragrance material holding member 200. Therefore, the fragrance material holding member 200 can be rotated with respect to the introduction port 522b by rotating the rotation transfer unit 510. Note that a locking groove may be provided on the tubular part 512 side, and a locking projection may be provided on the fragrance material holding member 200 side.

The locking projection 512a of the tubular part 512 and the locking groove 230 of the fragrance material holding member 200 are an example of a mechanism having a function of transferring rotation of the rotation transfer unit 510 to the fragrance material holding member 200, and a mechanism for implementing the function is not limited to this example. For example, the function may be implemented by lightly press-fitting the fragrance material holding member 200 to the tubular part 512, in which case the locking projection 512a and the locking groove 230 may be omitted from the configuration of the rotation mechanism 501 and the fragrance material holding member 200. In addition, the function may be implemented in the following manner: the shape of a transverse section of the fragrance material holding member 200 is set to a shape other than a circle, such as a polygon or an ellipse, and the shape of a portion of the tubular part 512 that is fitted to the fragrance material holding member 200 is set to a shape corresponding to the fragrance material holding member 200, thereby preventing relative rotation of the fragrance material holding member 200 and the tubular part 512.

A rear end face of the rotation transfer unit 510 is provided with a ring-shaped projection 518 projecting and covering an outer circumferential part of the front end side of the large diameter part 522 of the air introduction unit 520. The outer circumferential part of the front end side of the large diameter part 522 is fitted to an inner circumferential part of the ring-shaped projection 518. The ring-shaped projection 518 functions as a guide for rotation of the rotation transfer unit 510 with respect to the air introduction unit 520. In addition, a protrusion 518a projecting inwardly is provided on part of the inner circumferential part of the ring-shaped projection 518, and the protrusion 518a is locked in a ring-shaped groove 522f formed along an outer circumference of the large diameter part 522. Thus, the fragrance material holding member 200 and the rotation transfer unit 510 can be rotated with respect to the air introduction unit 520, without the rotation transfer unit 510 moving in the axial direction relatively with respect to the air introduction unit 520.

A rotation axis of the rotation of the fragrance material holding member 200 and the rotation transfer unit 510 substantially coincides with central axes of the fragrance material holding member 200, the rotation transfer unit 510, and the air introduction unit 520. A movable range of the member in the rotation by the rotation mechanism 500 can be made small by the fragrance material holding member 200, the tubular part 512 of the rotation transfer unit 510, and the large diameter part 522 of the air introduction unit 520 having tubular shapes or cylindrical shapes with central axes substantially coinciding with each other. However, the shapes of the fragrance material holding member 200, the tubular part 512 of the rotation transfer unit 510, and the large diameter part 522 of the air introduction unit 520 are not particularly limited.

The function as a guide for rotation of the rotation transfer unit 510 with respect to the air introduction unit 520 may be implemented by the small diameter part 524 of the air introduction unit 520 inserted into the opening 514a of the bottom part 514 and the inside of the inner circumferential part of the fragrance material holding member 200. In that case, the small diameter part 524 is fitted to the opening 514a of the bottom part 514 and the inner circumferential part of the fragrance material holding member 200, and the ring-shaped projection 518 may be omitted from the configuration of the rotation mechanism 501.

The rotation mechanism 501 according to the first example makes the rotation transfer unit 510 rotatable with respect to the air introduction unit 520, and is capable of rotating the fragrance material holding member 200 with respect to the air introduction unit 520, which is a member provided with the introduction port 522b, in a manner that the holding passage 210 that communicates with the introduction port 522b is switched. The plurality of holding passages 210 of the fragrance material holding member 200 are provided, for example, on a circumference around a rotation axis of relative rotation the air introduction unit 520 and the fragrance material holding member 200 by the rotation mechanism 501. Specifically, the plurality of holding passages 210 of the fragrance material holding member 200 are provided on a circumference around the central axis of the fragrance material holding member 200. Here, the fragrance material holding member 200 rotates around the central axis of the fragrance material holding member 200. Therefore, the holding passage 210 that communicates with the introduction port 522b can be switched by rotating the fragrance material holding member 200 with respect to the air introduction unit 520.

The holding passages 210 may be caused to hold different types of fragrance materials, in which case a fragrance provided by the fragrance providing device 1 can be switched by switching the holding passage 210 that communicates with the introduction port 522b. Note that the holding passages 210 may be caused to hold the same type of fragrance material. For example, duration of each fragrance material can be set appropriately in accordance with the frequency of use of each fragrance material by causing a larger number of holding passages 210 to hold a fragrance material used with higher frequency.

As described above, according to the fragrance providing device 1 according to the present embodiment, supply of air to a plurality of spaces each holding a fragrance material can be implemented by one airflow source, which can suppress an increase in the size of the device caused by an increase in the number of airflow sources in the case where the number of the spaces is increased. Hence, the device can be reduced in size.

Note that in the case where the lid 100 is fixed with respect to the fragrance material holding member 200, the lid 100 rotates with the rotation of the fragrance material holding member 200. In this case, the lid 100 is provided with discharge ports 110 the same in number as the holding passages 210, and each discharge port 110 is provided to communicate with a front end part of the corresponding holding passage 210. On the other hand, in the case where the lid 100 is fixed with respect to the rotation transfer unit 510, the fragrance material holding member 200 rotates with respect to the lid 100. In this case, the lid 100 is provided with one discharge port 110, and the one discharge port 110 is provided to communicate with the holding passage 210a that communicates with a front end part of the introduction port 522b.

In addition, as described above, the fragrance material holding member 200 has a tubular shape whose central axis substantially coincides with a rotation axis of relative rotation of the air introduction unit 520 and the fragrance material holding member 200. Thus, a movable range of the member in switching of the holding passage 210 that communicates with the introduction port 522b can be made small, which enables a further reduction in the size of the device.

The rotation mechanism 500 includes a positioning mechanism that determines a rotation angle of relative rotation of the air introduction unit 520 and the fragrance material holding member 200 in a manner that the introduction port 522b communicates with the holding passage 210. Specifically, the positioning mechanism includes a locking member that locks the air introduction unit 520 or the fragrance material holding member 200, and an urging member that urges the locking member. A steel ball 522c illustrated in FIG. 7 is an example of a locking member that locks the fragrance material holding member 200 via the rotation transfer unit 510, and a spring 522d is an example of an urging member.

As illustrated in FIGS. 6 and 7, a recess 516 is provided in a portion of the rear end face of the rotation transfer unit 510 that faces the step between the large diameter part 522 and the small diameter part 524 of the air introduction unit 520. In addition, the steel ball 522c and the spring 522d are provided at the step between the large diameter part 522 and the small diameter part 524 of the air introduction unit 520. The spring 522d is accommodated in a hole 522e made in the axial direction of the air introduction unit 520 that is formed at the step between the large diameter part 522 and the small diameter part 524, and the steel ball 522c is provided on the front end side of the spring 522d. For example, two pairs of the spring 522d and the steel ball 522c are provided as illustrated in FIG. 7. Note that the number of the pairs may be another number equal to or greater than 1. Recesses 516 the same in number as the number of pairs of the spring 522d and the steel ball 522c are provided for each holding passage 210. An arrangement of the recesses 516 is set in accordance with a position of each holding passage 210 in the fragrance material holding member 200 in a circumferential direction.

Specifically, the arrangement of the recesses 516 on the rear end face of the rotation transfer unit 510 is set in a manner that one of the recesses 516 is located on the front end side of the steel ball 522c in a state where the introduction port 522b communicates with the holding passage 210a. Therefore, in the case where the introduction port 522b communicates with one of the plurality of holding passages 210, the steel ball 522c is pressed against the recess 516 by urging force of the spring 522d, so that the rotation transfer unit 510 is positioned with respect to the air introduction unit 520. Thus, switching of the holding passage 210 that communicates with the introduction port 522b can be performed more easily.

On the other hand, the arrangement of the recesses 516 on the rear end face of the rotation transfer unit 510 is set in a manner that none of the recesses 516 is located on the front end side of the steel ball 522c in a state where the introduction port 522b communicates with none of the plurality of holding passages 210. Therefore, in the case where the introduction port 522b communicates with none of the plurality of holding passages 210, the steel ball 522c is accommodated inside the hole 522e together with the spring 522d; thus, rotation of the rotation transfer unit 510 with respect to the air introduction unit 520 can be performed smoothly.

In addition, a direction in which the locking member is urged may be a direction intersecting a rotation axis of relative rotation of the air introduction unit 520 and the fragrance material holding member 200. For example, the function of the positioning mechanism mentioned above may be implemented in the following manner: the locking member and the urging member are provided on the outer circumference side of the rotation transfer unit 510, and the locking member is urged in a radial direction of the rotation transfer unit 510. In that case, for example, an outer circumferential part of the rotation transfer unit 510 may be provided with a recess.

2-2. Second Example

The first example in which the rotation mechanism 501 is capable of rotating the fragrance material holding member 200 with respect to the air introduction unit 520, which is a member provided with the introduction port 522b, has been described, but the configuration of the rotation mechanism is not limited to this example, and the rotation mechanism may be capable of rotating the member provided with the introduction port with respect to the fragrance material holding member. Described below with reference to FIGS. 9 and 10 is a second example in which the rotation mechanism is capable of rotating the member provided with the introduction port with respect to the fragrance material holding member.

Figure 9:
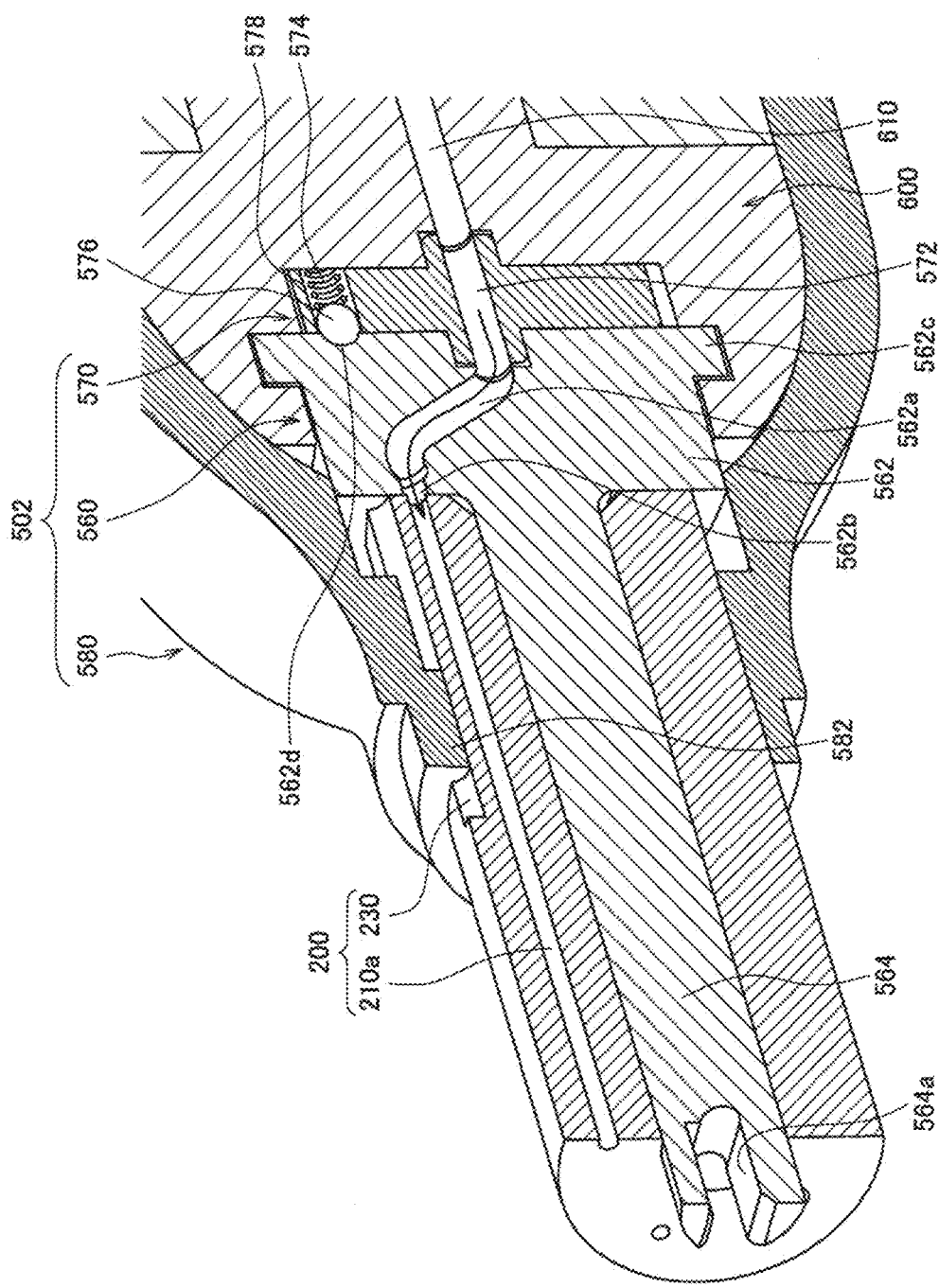
FIG. 9 is an explanatory diagram illustrating an example of a configuration of a fragrance material holding member and a rotation mechanism according to a second example.
Figure 10:
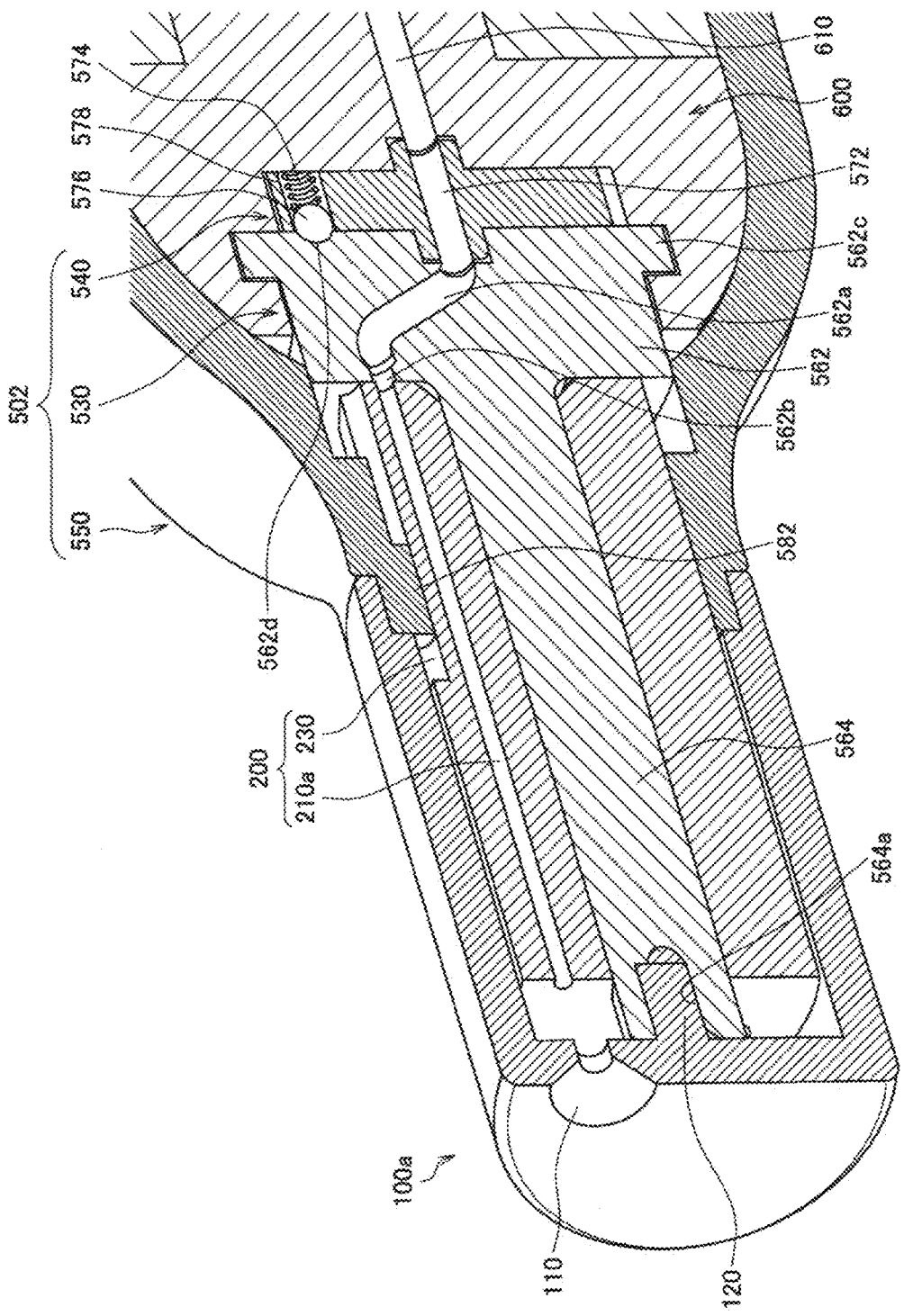
FIG. 10 is an explanatory diagram illustrating the example of the configuration of the fragrance material holding member and the rotation mechanism according to the second example.

FIGS. 9 and 10 are explanatory diagrams illustrating an example of a configuration of the fragrance material holding member 200 and a rotation mechanism 502 according to the second example. FIG. 9 is an explanatory diagram from which description of a lid 100a is omitted, and FIG. 10 is an explanatory diagram including description of the lid 100a. As illustrated in FIGS. 9 and 10, the rotation mechanism 502 according to the second example includes an air introduction unit 560, a positioning unit 570, and a housing 580. In the rotation mechanism 502 according to the second example, the air introduction unit 560 is rotatable with respect to the fragrance material holding member 200. Details of such a rotation mechanism 502 are described below.

The air introduction unit 560 includes a large diameter part 562 located on the rear end side and a small diameter part 564 that is a projecting part provided on a central part of the front end side of the large diameter part 562 and projecting in a front end direction. The large diameter part 562 and the small diameter part 564 each have a substantially tubular shape, for example. The large diameter part 522 is provided with a flow channel 562a for guiding the air supplied from the air pump 300 to the holding passage 210a. A rear end part of the flow channel 562a communicates with a flow channel 572 provided in the positioning unit 570. In addition, a rear end part of the flow channel 572 provided in the positioning unit 570 communicates with a front end part of the flow channel 610 of the chassis 600. Thus, the air supplied from the air pump 300 is sent to the flow channel 562a via the flow channel 610 and the flow channel 572. A front end part of the flow channel 562a is provided with an introduction port 562b that communicates with the holding passage 210a and introduces the air supplied from the air pump 300 to the holding passage 210a. The introduction port 562b may communicate with the holding passage 210a via another flow channel.

In addition, a rear end part of the large diameter part 562 is provided with a flange 562c projecting in an outer circumferential direction. The chassis 600 is provided with a depression having a shape corresponding to the flange 562c, and movement of the air introduction unit 560 in a translation direction is constrained by the flange 562c being supported by the depression of the chassis 600. In addition, the depression may function as a guide for rotation of the air introduction unit 560 with respect to the chassis 600. Thus, the air introduction unit 560 can be rotated with respect to the chassis 600.

The small diameter part 564 is inserted into the inside of the inner circumferential part of the fragrance material holding member 200, and is provided to extend in the axial direction of the fragrance material holding member 200. As illustrated in FIG. 10, a front end part of the small diameter part 564 that penetrates the fragrance material holding member 200 is provided with a depression 564a into which a protrusion 120 projecting in a rear end direction from a rear end face of the lid 100a that separates the fragrance material holding member 200 from the outside is inserted. Thus, as illustrated in FIG. 10, the air introduction unit 560 can be rotated with respect to the fragrance material holding member 200 by rotating the lid 100a in a state where the protrusion 120 of the lid 100a is inserted into the depression 564a of the small diameter part 564.

The function as a guide for rotation of the air introduction unit 560 with respect to the chassis 600 may be implemented by the small diameter part 564 of the air introduction unit 560 inserted into the inside of the inner circumferential part of the fragrance material holding member 200. In that case, the small diameter part 564 is fitted to the inner circumferential part of the fragrance material holding member 200.

The housing 580 is a member that accommodates other members constituting the fragrance providing device, excluding part of the front end side of the fragrance material holding member 200, and the chassis 600 is fixed inside the housing 580. A rear end part of the lid 100a is connected to a front end part of the housing 580. Thus, the lid 100a and the housing 580 accommodate the other members constituting the fragrance providing device. Here, the lid 100a is configured to be freely rotatable with respect to the housing 580.

In addition, as illustrated in FIGS. 9 and 10, an inner circumferential part of the front end part of the housing 580 is provided with a locking projection 582 projecting inwardly. The locking projection 582 is provided to extend along the axial direction of the fragrance material holding member 200, for example. The locking projection 582 is fitted to the locking groove 230 provided on an outer circumferential part of the fragrance material holding member 200 to extend along the axial direction of the fragrance material holding member 200. This makes it possible to prevent rotation of the fragrance material holding member 200 in the case where the air introduction unit 560 is rotated, and to rotate the air introduction unit 560 with respect to the fragrance material holding member 200. Therefore, the introduction port 562b of the air introduction unit 560 can be rotated with respect to the fragrance material holding member 200. Note that a locking groove may be provided on the housing 580 side, and a locking projection may be provided on the fragrance material holding member 200 side.

The locking projection 582 of the housing 580 and the locking groove 230 of the fragrance material holding member 200 are an example of a mechanism having a function of preventing rotation of the fragrance material holding member 200 in the case where the air introduction unit 560 is rotated, and a mechanism for implementing the function is not limited to this example. For example, the function may be implemented by lightly press-fitting the fragrance material holding member 200 to the housing 580, in which case the locking projection 582 and the locking groove 230 may be omitted from the configuration of the rotation mechanism 502 and the fragrance material holding member 200. In addition, the function may be implemented in the following manner: the shape of a transverse section of the fragrance material holding member 200 is set to a shape other than a circle, such as a polygon or an ellipse, and the shape of a portion of the housing 580 that is fitted to the fragrance material holding member 200 is set to a shape corresponding to the fragrance material holding member 200, thereby preventing relative rotation of the fragrance material holding member 200 and the housing 580.

A rotation axis of the rotation of the air introduction unit 560 substantially coincides with central axes of the fragrance material holding member 200 and the air introduction unit 560. A movable range of the member in the rotation by the rotation mechanism 502 can be made small by the fragrance material holding member 200 and the small diameter part 564 and the large diameter part 562 of the air introduction unit 560 having tubular shapes or cylindrical shapes with central axes substantially coinciding with each other. However, the shapes of the fragrance material holding member 200 and the small diameter part 564 and the large diameter part 562 of the air introduction unit 560 are not particularly limited.

The rotation mechanism 502 according to the second example makes the air introduction unit 560 rotatable with respect to the fragrance material holding member 200, and is capable of rotating the air introduction unit 560, which is a member provided with the introduction port 562b, with respect to the fragrance material holding member 200 in a manner that the holding passage 210 that communicates with the introduction port 562b is switched. The plurality of holding passages 210 of the fragrance material holding member 200 are provided, for example, on a circumference around a rotation axis of relative rotation the air introduction unit 560 and the fragrance material holding member 200 by the rotation mechanism 502. Specifically, the plurality of holding passages 210 of the fragrance material holding member 200 are provided on a circumference around the central axis of the fragrance material holding member 200. Here, the air introduction unit 560 rotates around the central axis of the fragrance material holding member 200. Therefore, the holding passage 210 that communicates with the introduction port 562b can be switched by rotating the air introduction unit 560 with respect to the fragrance material holding member 200. Thus, in the case where the holding passages 210 are caused to hold different types of fragrance materials, a fragrance provided by the fragrance providing device 1 can be switched. Note that the holding passages 210 may be caused to hold the same type of fragrance material.

The positioning unit 570 has a function as a positioning mechanism that determines a rotation angle of relative rotation of the air introduction unit 560 and the fragrance material holding member 200 in a manner that the introduction port 562b communicates with the holding passage 210. Specifically, the function as the positioning mechanism is implemented by a locking member that locks the air introduction unit 560 or the fragrance material holding member 200, and an urging member that urges the locking member. A steel ball 576 illustrated in FIGS. 9 and 10 is an example of a locking member that locks the air introduction unit 560, and a spring 574 is an example of an urging member.

As illustrated in FIGS. 9 and 10, a rear end face of the air introduction unit 560 is provided with a recess 562d. In addition, a front end face of the positioning unit 570 is provided with the steel ball 576 and the spring 574. The spring 574 is accommodated in a hole 578 made in the axial direction of the air introduction unit 560, and the steel ball 576 is provided on the front end side of the spring 574. For example, one pair of the spring 574 and the steel ball 576 is provided as illustrated in FIGS. 9 and 10. Note that the number of the pairs may be another number equal to or greater than 2. Recesses 562d the same in number as the number of pairs of the spring 574 and the steel ball 576 are provided for each holding passage 210. An arrangement of the recesses 562d is set in accordance with a position of each holding passage 210 in the fragrance material holding member 200 in a circumferential direction.

Specifically, the arrangement of the recesses 562d on the rear end face of the air introduction unit 560 is set in a manner that one of the recesses 562d is located on the front end side of the steel ball 576 in a state where the introduction port 562b communicates with the holding passage 210a. Therefore, in the case where the introduction port 562b communicates with one of the plurality of holding passages 210, the steel ball 576 is pressed against the recess 562d by the urging force of the spring 574, so that the air introduction unit 560 is positioned with respect to the positioning unit 570. Here, the positioning unit 570 is fixed with respect to the chassis 600. In addition, the fragrance material holding member 200 is fixed with respect to the chassis 600 via the housing 580. Therefore, by the function of the positioning unit 570 as the positioning mechanism, the air introduction unit 560 is positioned with respect to the fragrance material holding member 200. Thus, switching of the holding passage 210 that communicates with the introduction port 562b can be performed more easily.

On the other hand, the arrangement of the recesses 562d on the rear end face of the air introduction unit 560 is set in a manner that none of the recesses 562d is located on the front end side of the steel ball 576 in a state where the introduction port 562b communicates with none of the plurality of holding passages 210. Therefore, in the case where the introduction port 562b communicates with none of the plurality of holding passages 210, the steel ball 576 is accommodated inside the hole 578 together with the spring 574; thus, rotation of the air introduction unit 560 with respect to the positioning unit 570 and the fragrance material holding member 200 can be performed smoothly.

In addition, a direction in which the locking member is urged may be a direction intersecting a rotation axis of relative rotation of the air introduction unit 560 and the fragrance material holding member 200. For example, the function of the positioning mechanism mentioned above may be implemented in the following manner: the locking member and the urging member are provided on the outer circumference side of the air introduction unit 560, and the locking member is urged in a radial direction of the air introduction unit 560. In that case, for example, an outer circumferential part of the air introduction unit 560 may be provided with a recess.

In addition, the positioning unit 570 is provided with the flow channel 572 whose rear end part communicates with the front end part of the flow channel 610 of the chassis 600 and whose front end part communicates with the flow channel 562a of the air introduction unit 560. The air supplied from the air pump 300 is sent from the flow channel 610 of the chassis 600 to the flow channel 562a of the air introduction unit 560 via the flow channel 572 of the positioning unit 570.

3. MODIFICATION EXAMPLES

Now, fragrance providing devices according to modification examples will be described with reference to FIGS. 11 to 14, the fragrance providing devices facilitating recognition of which of a plurality of fragrance materials is selected as a fragrance material corresponding to a fragrance provided by the fragrance providing device.

Figure 11:
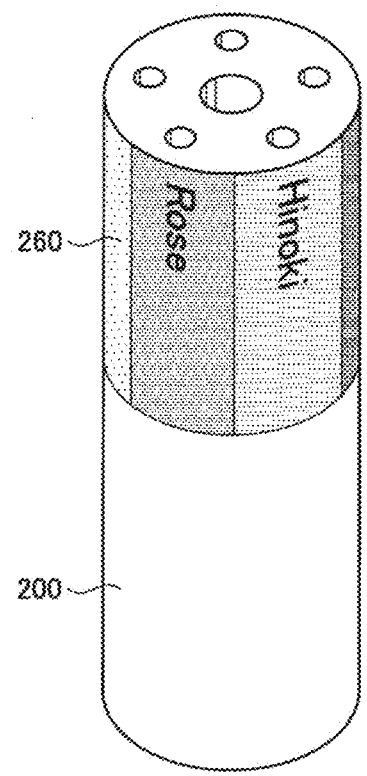
FIG. 11 is an explanatory diagram illustrating an example of a configuration of a label according to a first modification example.

First, a first modification example is described with reference to FIGS. 11 to 13. In the first modification example, as a rotation mechanism, the rotation mechanism 501 according to the above-described first example, which is capable of rotating the fragrance material holding member with respect to the member provided with the introduction port, is applied, for example. FIG. 11 is an explanatory diagram illustrating an example of a configuration of a label 260 according to the first modification example. In the first modification example, on an outer circumferential surface of the fragrance material holding member 200, types of respective fragrance materials held by the plurality of holding passages 210 are indicated. For example, as illustrated in FIG. 11, the outer circumferential surface of the fragrance material holding member 200 is provided with the label 260 indicating types of fragrance materials held by the holding passages 210. On the label 260 is written, at a position that substantially coincides with a position in a circumferential direction where each holding passage 210 is provided in the fragrance material holding member 200, a type of a fragrance material held by the corresponding holding passage 210.

Figure 12:
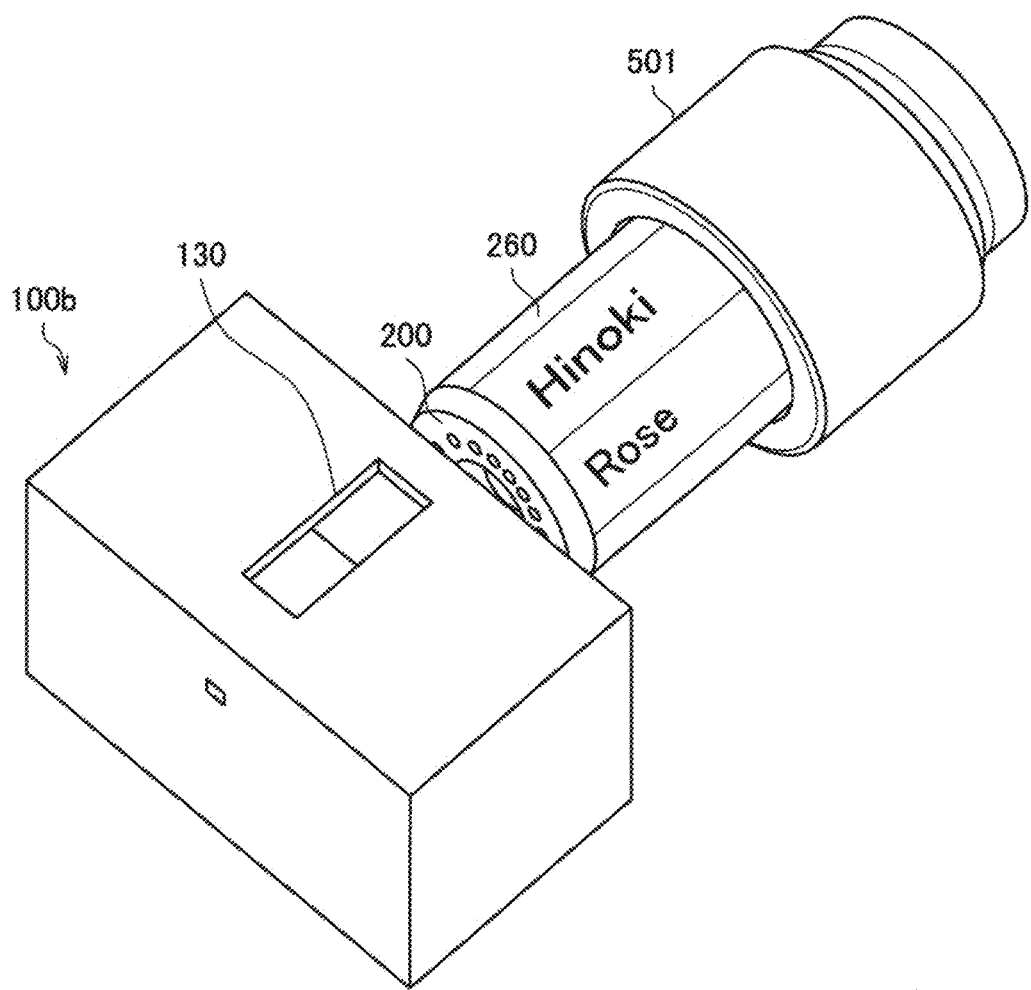
FIG. 12 is an explanatory diagram illustrating an example of a configuration of a fragrance material holding member, a lid, and a rotation mechanism according to the first modification example.
Figure 13:
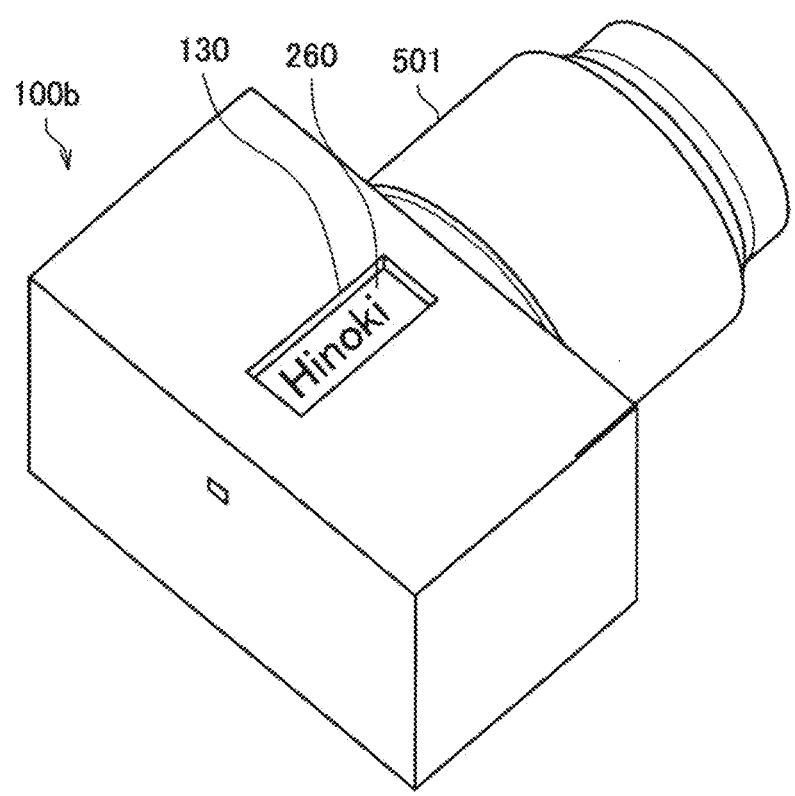
FIG. 13 is an explanatory diagram illustrating the example of the configuration of the fragrance material holding member, the lid, and the rotation mechanism according to the first modification example.

FIGS. 12 and 13 are explanatory diagrams illustrating an example of a configuration of the fragrance material holding member 200, a lid 100b, and the rotation mechanism 501 according to the first modification example. FIG. 12 illustrates a state before the fragrance material holding member 200 is covered by the lid 100b, and FIG. 13 illustrates a state after the fragrance material holding member 200 is covered by the lid 100b. An outer circumferential part of the lid 100b according to the first modification example is provided with an opening 130. The lid 100b is an example of a cover member according to the present disclosure. As illustrated in FIG. 13, the position and size of the opening 130 in the lid 100b are set in a manner that a type of a fragrance material written on the label 260 can be seen from the outside via the opening 130 in a state after the fragrance material holding member 200 is covered by the lid 100b. The shape of the outline of the lid 100b may be, but is not particularly limited to, a rectangular parallelepiped as illustrated in FIGS. 12 and 13.

In the first modification example, the rotation mechanism 501 is capable of relatively rotating the lid 100b and the fragrance material holding member 200. Specifically, in the first modification example, the rotation mechanism 501 is capable of rotating the fragrance material holding member 200 with respect to the lid 100b. On the outer circumferential surface of the fragrance material holding member 200, a type of a fragrance material held by the holding passage 210 that communicates with the introduction port 522b is indicated at a position facing the opening 130. Thus, the type of the fragrance material held by the holding passage 210 that communicates with the introduction port 522b can be seen via the opening 130, which facilitates recognition of which of a plurality of fragrance materials is selected as a fragrance material corresponding to a fragrance provided by the fragrance providing device. Note that in the first modification example, the rotation mechanism 502 according to the above-described second example may also be applied as a rotation mechanism.

Now, a second modification example in which the rotation mechanism 502 according to the above-described second example, which is capable of rotating the member provided with the introduction port with respect to the fragrance material holding member, is applied as a rotation mechanism will be described with reference to FIG. 14.

FIG. 14 is an explanatory diagram illustrating an example of a configuration of a fragrance providing device 1b according to the second modification example. In the fragrance providing device 1b according to the second modification example, an outer circumferential part of a lid 100c is provided with the opening 130, unlike the lid 100a according to the above-described second example. In the second modification example, the rotation mechanism 502 is capable of rotating the lid 100c with respect to the fragrance material holding member 200. Also in the second modification example, on the outer circumferential surface of the fragrance material holding member 200, a type of a fragrance material held by the holding passage 210 that communicates with the introduction port 562b is indicated at a position facing the opening 130, as in the first modification example. Thus, an effect similar to that in the first modification example can be obtained according to the second modification example as well. Note that as illustrated in FIG. 14, an outer circumferential part of the housing 580 may be provided with a button 584 for pressing the switch 700. The switch 700 is configured to be pressed by pressing the button 584.

4. CONCLUSION

As described above, according to an embodiment of the present disclosure, the rotation mechanism 500 is capable of relatively rotating the fragrance material holding member 200 and a member provided with an introduction port that communicates with part of the plurality of holding passages 210 and introduces the air supplied from the air pump 300 to part of the holding passages 210, in a manner that part of the holding passages 210 that communicates with the introduction port is switched. Thus, supply of air to a plurality of spaces each holding a fragrance material can be implemented by one airflow source. This can suppress an increase in the size of the device caused by an increase in the number of airflow sources in the case where the number of the spaces is increased. Hence, the device can be reduced in size.

Described above is an example in which one holding passage 210 among the plurality of holding passages 210 communicates with an introduction port that introduces the air supplied from the air pump 300 to the holding passage 210; however, the technical scope of the present disclosure is not limited to this example. For example, the introduction port may communicate with two or more holding passages 210 at the same time.

Described above is an example in which the rear end part of the holding passage 210 that communicates with the introduction port is provided on the rear end face of the fragrance material holding member 200; however, the technical scope of the present disclosure is not limited to this example. For example, the rear end part of the holding passage 210 may be formed on the outer circumferential surface of the fragrance material holding member 200. In that case, the air flow channel between the air pump 300 and the holding passage 210 is set to correspond to an arrangement of the rear end part of the holding passage 210.

Described above is an example in which the front end part of the holding passage 210 that communicates with the discharge port 110 of the lid 100 is provided on the front end face of the fragrance material holding member 200; however, the technical scope of the present disclosure is not limited to this example. For example, the front end part of the holding passage 210 may be formed on the outer circumferential surface of the fragrance material holding member 200. In that case, an arrangement of the discharge port 110 of the lid 100 is set to correspond to an arrangement of the front end part of the holding passage 210.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A fragrance providing device including:

a fragrance material holding member in which a plurality of holding passages each holding a fragrance material are provided to penetrate the fragrance material holding member; and a rotation mechanism capable of relatively rotating the fragrance material holding member and a member provided with an introduction port that communicates with part of the plurality of holding passages and introduces air supplied from an airflow source to the part of the holding passages, in a manner that the part of the holding passages that communicates with the introduction port is switched.

(2)

The fragrance providing device according to (1), in which the plurality of holding passages are provided on a circumference around a rotation axis of relative rotation of the member provided with the introduction port and the fragrance material holding member.

(3)

The fragrance providing device according to (1) or (2), in which the fragrance material holding member has a tubular shape whose central axis substantially coincides with a rotation axis of relative rotation of the member provided with the introduction port and the fragrance material holding member.

(4)

The fragrance providing device according to any one of (1) to (3), in which the rotation mechanism is capable of rotating the fragrance material holding member with respect to the member provided with the introduction port.

(5)

The fragrance providing device according to (4), in which the rotation mechanism includes a rotation transfer unit that holds the fragrance material holding member and a mechanism that transfers rotation of the rotation transfer unit to the fragrance material holding member, and is capable of rotating the fragrance material holding member and the rotation transfer unit with respect to the member provided with the introduction port.

(6)

The fragrance providing device according to any one of (1) to (3), in which the rotation mechanism is capable of rotating the member provided with the introduction port with respect to the fragrance material holding member.

(7)

The fragrance providing device according to (6), in which the member provided with the introduction port includes a projecting part that penetrates the fragrance material holding member, and a front end part of the projecting part is provided with a depression into which a protrusion provided on a lid that separates the fragrance material holding member from an outside is inserted.

(8)

The fragrance providing device according to any one of (1) to (7), in which the rotation mechanism includes a positioning mechanism that determines a rotation angle of relative rotation of the member provided with the introduction port and the fragrance material holding member in a manner that the introduction port communicates with the part of the holding passages.

(9)

The fragrance providing device according to (8), in which the positioning mechanism includes a locking member that locks the member provided with the introduction port or the fragrance material holding member, and an urging member that urges the locking member.

(10)

The fragrance providing device according to any one of (1) to (9), including a cover member that covers the fragrance material holding member and whose outer circumferential part is provided with an opening, in which the rotation mechanism is capable of relatively rotating the cover member and the fragrance material holding member, and on an outer circumferential surface of the fragrance material holding member, a type of the fragrance material held by the part of the holding passages that communicates with the introduction port is indicated at a position facing the opening.

REFERENCE SIGNS LIST 1, 1a, 1b fragrance providing device
100, 100a, 100b, 100c lid
110 discharge port
120 protrusion
130 opening
200 fragrance material holding member
210, 210a, 210b holding passage
230 locking groove
260 label
300 air pump
310 motor
400 battery
500, 501, 502 rotation mechanism
510 rotation transfer unit
512 tubular part
512a locking projection
514 bottom part
514a opening
514b flow channel
518 ring-shaped projection
518a protrusion
520 air introduction unit
522 large diameter part
522a flow channel
522b introduction port
522c steel ball
522d spring
522e hole
522f ring-shaped groove
524 small diameter part
560 air introduction unit
562 large diameter part
562a flow channel
562b introduction port
562c flange
564 small diameter part
564a depression
570 positioning unit
572 flow channel
574 spring
576 steel ball
578 hole
580 housing
582 locking projection
584 button 600 chassis
610 flow channel
700, 710 switch
800 substrate

The invention claimed is:

1. A fragrance providing device comprising:
a fragrance material holding member in which a plurality of holding passages each holding a fragrance material are provided to penetrate the fragrance material holding member;
a member provided with an introduction port that communicates with part of the plurality of holding passages and introduces air supplied from an airflow source to the part of the holding passages;
a rotation mechanism capable of relatively rotating the fragrance material holding member and the member provided with the introduction port in a manner that the part of the plurality of holding passages that communicates with the introduction port is switched; and
a cover member that separates the fragrance material holding member from an outside and is provided with a discharge port that communicates with a front end part of the part of the holding passages, wherein
the member provided with the introduction port is inserted into an inside of an inner circumferential part of the fragrance material holding member to be engaged with the cover member, and
the rotation mechanism is capable of relatively rotating the fragrance material holding member, the member provided with the introduction port, and the cover member.

2. The fragrance providing device according to claim 1, wherein the plurality of holding passages are provided on a circumference around a rotation axis of relative rotation of the member provided with the introduction port and the fragrance material holding member.

3. The fragrance providing device according to claim 1, wherein the fragrance material holding member has a tubular shape whose central axis substantially coincides with a rotation axis of relative rotation of the member provided with the introduction port and the fragrance material holding member.

4. The fragrance providing device according to claim 1, wherein the rotation mechanism is capable of rotating the fragrance material holding member with respect to the member provided with the introduction port.

5. The fragrance providing device according to claim 4, wherein the rotation mechanism includes a rotation transfer unit that holds the fragrance material holding member and a mechanism that transfers rotation of the rotation transfer unit to the fragrance material holding member, and is capable of rotating the fragrance material holding member and the rotation transfer unit with respect to the member provided with the introduction port.

6. The fragrance providing device according to claim 1, wherein the rotation mechanism is capable of rotating the member provided with the introduction port with respect to the fragrance material holding member.

7. The fragrance providing device according to claim 6, wherein
the member provided with the introduction port includes a projecting part that penetrates the fragrance material holding member, and
a front end part of the projecting part is provided with a depression into which a protrusion provided on the cover member is inserted.

8. The fragrance providing device according to claim 1, wherein the rotation mechanism includes a positioning mechanism that determines a rotation angle of relative rotation of the member provided with the introduction port and the fragrance material holding member in a manner that the introduction port communicates with the part of the holding passages.

9. The fragrance providing device according to claim 8, wherein the positioning mechanism includes a locking member that locks the member provided with the introduction port or the fragrance material holding member, and an urging member that urges the locking member.

10. The fragrance providing device according to claim 1, wherein
the cover member covers the fragrance material holding member,
an outer circumferential part of the cover member is provided with an opening,
the rotation mechanism is capable of relatively rotating the cover member and the fragrance material holding member, and
on an outer circumferential surface of the fragrance material holding member, a type of the fragrance material held by the part of the holding passages that communicates with the introduction port is indicated at a position facing the opening.

11. The fragrance providing device according to claim 1, wherein
the cover member is provided with a protrusion projecting toward the fragrance material holding member side,
the member provided with the introduction port includes a projecting part that is inserted into the inside of the inner circumferential part of the fragrance material holding member and is provided to extend in an axial direction of the fragrance material holding member, and
the protrusion provided on the cover member is engaged with a front end part of the projecting part.

12. The fragrance providing device according to claim 1, wherein the fragrance material is held in a state of adhering to an inner surface of the holding passage.

13. The fragrance providing device according to claim 12, wherein the air flows from a rear end side to a front end side of the holding passage.

14. The fragrance providing device according to claim 1, further comprising
an accommodation member that accommodates at least part of the fragrance material holding member,
wherein an outer circumferential part of the fragrance material holding member is provided with a locking projection or a locking groove that prevents relative rotation of the fragrance material holding member and the accommodation member by fitting to an inner circumferential part of the accommodation member.

15. The fragrance providing device according to claim 9, further comprising
a plurality of recesses provided for the plurality of holding passages, wherein
the rotation angle is fixed by the locking member being pressed against the recess by the urging member, and
an arrangement of the recesses is set in accordance with a position of each of the plurality of holding passages in the fragrance material holding member in a circumferential direction.

16. The fragrance providing device according to claim 1, further comprising
the airflow source, wherein the airflow source is an air pump that includes a diaphragm and performs air blowing by deforming the diaphragm.

* * * * *